United States Patent [19]

Knaack et al.

[11] Patent Number: 5,320,963
[45] Date of Patent: Jun. 14, 1994

[54] BIOREACTOR FOR THE PERFUSION CULTURE OF CELLS

[75] Inventors: Christian Knaack, Montréal; Gérald André, Ile Bizard; Claude Chavarie, Montréal, all of Canada

[73] Assignee: National Research Council of Canada, Ottawa, Canada

[21] Appl. No.: 981,490

[22] Filed: Nov. 25, 1992

[51] Int. Cl.⁵ .............................................. C12M 1/10
[52] U.S. Cl. ..................................... 435/286; 435/315; 435/316; 210/615; 210/619
[58] Field of Search ............... 435/284, 286, 315, 316, 435/813; 210/615, 619

[56] References Cited

U.S. PATENT DOCUMENTS

| | | | |
|---|---|---|---|
| 2,083,348 | 6/1937 | Schöller et al. | 435/314 |
| 3,635,346 | 1/1972 | Zuckerman et al. | 210/208 |
| 4,335,215 | 6/1982 | Tolbert et al. | 435/241 |
| 4,748,123 | 5/1988 | Birch et al. | 435/261 |
| 4,814,278 | 3/1989 | Hamamoto et al. | 435/286 |

FOREIGN PATENT DOCUMENTS 0191356  8/1986  European Pat. Off. .
9106627  5/1991  PCT Int'l Appl. .

*Primary Examiner*—James C. Housel
*Assistant Examiner*—N. Bhat
*Attorney, Agent, or Firm*—Juliusz Szereszewski

[57] ABSTRACT

A bioreactor for perfusion culture of suspension cells has an inversely-conical tank which includes a cell culture zone and a cell settling zone disposed annularly relative to the cell culture zone in the upper region of the tank. The cell settling zone is adjacent to the conical walls of the tank and has a number of frustoconical lamellar elements. The two zones are separated with a partition which allows the zones to communicate only below the partition. Cell culture medium supplied to the culture zone overflows at the top of the settling zone after having passed through the settling zone between the lamellar elements. Due to the conical shape of the tank and the resulting shape of the settling zone, passages of upwardly increasing cross section are created in the settling zone thus enabling the settling of live cells in the settling zone and their return to the culture zone while the spent medium overflows. The design is relatively easy to scale up.

8 Claims, 1 Drawing Sheet

BIOREACTOR FOR THE PERFUSION CULTURE OF CELLS

FIELD OF THE INVENTION

This invention relates to a bioreactor for culturing cells in a perfusion mode, and more specifically, a conical bioreactor with a lamellar settler, for continuous perfusion culturing of suspension cells.

BACKGROUND OF THE INVENTION

In a perfusion culture of suspension cells (perfusion meaning a continuous flow of culture medium through a culture maintained at high cell density; suspension cells being cells which do not require a solid support to grow on), for example in the production of monoclonal antibodies or viral vaccines, fresh nutrients must be supplied continuously with concomitant removal of toxic metabolites and, ideally, selective removal of dead cells. Removing spent medium while retaining cells in a bioreactor presents a technical problem due to the small size of cells and an average cell density only slightly greater than that of the culture medium. Filtering, entrapment and micro-capsulation methods are all suitable for refreshing the culture environment at sufficient rates. However, these methods all share certain characteristic disadvantages, chief among which are accumulation of dead cells within the system and membrane bio-fouling, which hinder attempts at industrial-scale application. The above disadvantages have a considerable impact on the quantitative recovery of active product.

Known systems for selective removal of dead cells during perfusion culture are, with very few exceptions, based on cell sedimentation. For the reasons mentioned above (i.e. small cell size and equally small density difference between cells and culture medium), unit gravity is rarely considered sufficient. The effect of gravity is multiplied, either by the use of a centrifuge, or by exploiting the Boycott effect. This effect, quantified in 1920, is a finding of faster settling of suspended particles between closely spaced inclined surfaces than in vertical chambers.

In many cases, dead suspension cells have a smaller cell diameter than live cells of the same cell line. This difference in diameter translates into a proportional difference in sedimentation rate, which can be exploited for the selective removal of dead cells.

Certain existing sedimentation systems are based on laminar flow in a conical sedimenter while some others exploit so-called lamellar settlers. In most cases, the latter feature a series of parallel plates, inclined most often at 30° from the vertical, within a rectangular chamber. As fluid flows upwards between the parallel plates, particles settle onto the upper surfaces of the plates and slide toward the bottom of the chamber for collection.

B. C. Batt et al., Biotechnol. Prog., 6, 458–464, (1990) describe a continuous perfusion system consisting of a standard stirred-tank laboratory-scale bioreactor with a rectangular lamellar settler disposed above the former. Sato et al., J. Tiss. Cult. Meth. 8(4), pp. 167–171, 1983, developed an internal conical cell separator in which a tapered conical sedimentation chamber was affixed to the underside of the headplate of the bioreactor vessel.

A recently developed conical lamellar settler (M. Tyo, presentation at the 1989 annual AIChE meeting in Santa Barbara, Calif.; New Developments in Mammalian Cell Reactor Studies, Nov. 5–10, 1989), combines the advantages of conical and lamellar settlers. A conical settler is affixed to the top of a standard 250 ml spinner flask. The settler consists of a pair of concentric truncated cones with an innermost solid cone. As the cell suspension is pumped upwards from the reactor into and through the settler, the latter creates an annular flow passageway of increasing cross-sectional area with increasing distance from the lower apex. As a result, the vertical component of the liquid velocity decreases, which allows the sedimentation of cells and their collection on the upper surfaces of the truncated cones. Sedimented cells slide along these surfaces by gravity and return to the reactor, while partially clarified cell suspension (containing cells too small to have sedimented) is removed through the top of the settler. Because the settler has to occupy the entire available area at the top of the cylindrical reactor vessel, the scale-up of this design is very limited.

Hamamoto et al, U.S. Pat. No. 4,814,278 issued Mar. 21, 1989, describes an apparatus for perfusion cell culture, which has a cell culture zone and an annular cell settling zone disposed concentrically around the culture zone and separated therefrom by a partition allowing the two zones to communicate only below the partition. At any scale larger than a few liters, this design imposes aspect ratios in the culture zone which are unsuitable for the culture of animal cells. Thus the scale-up of this design is also severely limited.

There is still a need to develop a system which could offer, beside an efficiency at least comparable to known systems, a possibility of scale-up and a simpler design.

SUMMARY OF THE INVENTION

It is an object of this invention to provide an apparatus of a simple design which enables a perfusion culture of suspension cells at a relatively high cell density.

It is another object of this invention to provide an apparatus enabling spent culture medium to be withdrawn from the apparatus substantially free of live cells, without using a filter.

It is still another object of this invention to provide an apparatus in which the withdrawal of spent medium does not require pumping means.

According to the invention, there is provided an apparatus for perfusion cell culture comprising:

a cell culture tank having a suspension cell culture zone, a cell settling zone, an opening at the top of the tank for supplying a culture medium to said cell culture zone and an opening for discharging a spent culture medium from said settling zone, the settling zone being disposed in the upper portion of the tank coextensively, in a vertical direction, with a part of the cell culture zone, a partition disposed between said zones so as to enable said zones to communicate with each other only below said partition, wherein the tank has upwardly diverging side walls at least in the upper region of said tank which houses said settling zone, and the settling zone comprises means defining a plurality of angularly disposed passageways of upwardly increasing cross-sectional area.

In a preferred embodiment of the invention, the apparatus has substantially an inverted conical shape. The settling zone is preferably disposed between the upwardly diverging side walls and the partition, with the passageways being disposed substantially parallel to the side walls for an optimum use of space.

The passageways can be defined by a plurality of interspaced frustoconical lamellar elements having upwardly diverging surfaces for the cells to settle on.

To eliminate forced removal of the spent medium, it is preferable that the opening from the settling zone is disposed below a level defined by the top of the cell culture zone to enable the medium to overflow from the settling zone when the level of the medium rises in the cell culture zone, but above the upper level of the angular passageways so as to create a manifold area above said passageways.

In a preferred embodiment of the invention illustrated hereinbelow, the settling zone is disposed annularly around the cell culture zone in the upper region of a conical tank, and the culture zone comprises means defining a riser and a downcomer passage.

Further, the apparatus may comprise means for agitating the culture medium in the culture zone and means for supplying a culture-promoting gas to the cell culture zone.

BRIEF DESCRIPTION OF THE DRAWINGS

In the drawings in which like numerals correspond to same elements.

DETAILED DESCRIPTION OF THE PREFERRED EMBODIMENTS

Figure 1:
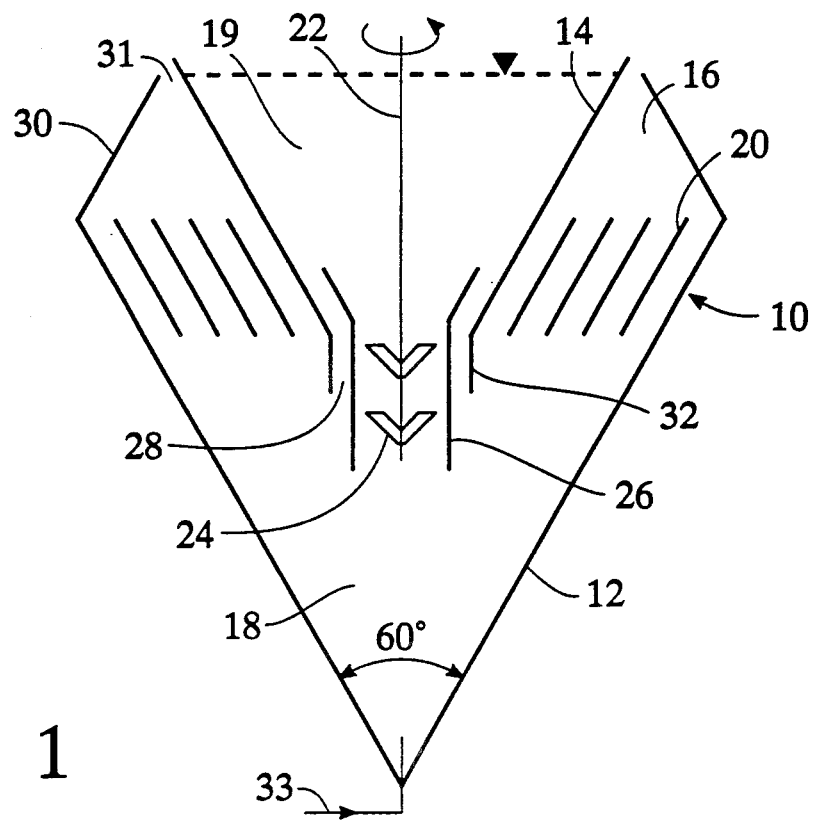
FIG. 1 is an axial cross-section of an embodiment of the apparatus of the invention.

Generally, the apparatus of the invention has a tank with upwardly diverging side walls at least in the upper, settling zone region of the tank. Preferably, for design and construction purposes, the tank has a conical shape as illustrated in the drawings. This feature is a departure from prior art designs where only the separator has a conical shape.

Four basic parameters are known to affect the performance of a sedimenter for living matter:

1) the area, perpendicular to fluid flow, of the entrance which determines the upward velocity of the fluid entering the sedimenter; if this upward velocity is too high, sedimenting cells cannot return to the reactor (culture zone), 2) the fluid residence time, 3) the mean cell residence time, and 4) the total area within the sedimenter which is available for cell settling.

The horizontal area of the entrance to a sedimenter attached to or included in a reactor has to be sized according to the reactor volume and the perfusion rate. The daily flow rate divided by the horizontal entrance area gives the velocity of the fluid entering the sedimenter. This velocity must be less than the terminal velocity (sedimentation rate) of a live cell. This constraint determines the entrance size of the sedimenter once a given reactor volume and a given maximum perfusion rate are chosen.

The above considerations impose certain restrictions on the design of a bioreactor. The entrance area must be found in the reactor while still leaving room for the agitation means and probes and without interfering with the overall mixing pattern.

In the case of a cylindrical reactor vessel, the increase of the sedimenter entrance area typically involves the increase of the radius of the vessel which in turn increases the reactor volume and thus the daily flow rate. To facilitate scale-up of animal cell bioreactors, it is best to maintain an approximately constant aspect ratio, the present rule of thumb being a ratio in a range between 1 and 1.5. As a result, the reactor volume grows as a cubic function of its linear dimensions while the sedimenter entrance area can only grow as a square function of the linear dimensions. In a cylindrical reactor geometry, at a vessel volume as low as 2 liters, one is faced with a situation where the minimum entrance size of the sedimenter, necessary for its proper functioning, is greater than the available entrance size at the top of the reactor.

In a conical reactor vessel of the invention, while the same geometrical relationships apply, the only parameter to change is the cone height (assuming that the cone angle is fixed). When H is increased, both the reactor volume and the available area for a sedimenter are increased, as long as the height h at which the sedimenter entrance is placed is increased as well, and especially if the riser and downcomer diameters are kept constant. Thus, while the same surface/volume limitation eventually limits the scale-up, the conical shape allows for a considerably wider margin of vessel volumes.

Turning now to the drawings, FIG. 1 shows an apparatus for continuous suspension cell culture. The apparatus has a tank 10 having inverted conical side wall 12 and open at the top. A partition 14 extending conically downwardly from the top of the tank 10 divides the inside of the tank into an annular settling zone 16 and a cell culture zone 18, 19. In the settling zone 16 there is mounted a number of frustoconical lamellar elements 20 spaced from each other, from the partition 14 and from the side wall 12 so as to define a corresponding number of inclined passageways. Because of the conical shape of the side wall 12, partition 14 and the lamellar elements 20 which, as shown in the drawings are disposed parallel to both the side wall and the partition 14 in its conical region, the passageways have upwardly increasing cross-sectional area.

An agitator 22 with an Archimedean screw 24 is mounted along the vertical axis of the tank 10 and a draft tube 26 is mounted concentrically with the agitator 22. The draft tube is partly co-extensive with the partition 14 and spaced therefrom so as to define an annular passage 28 therebetween, the passage serving as a downcomer for the medium in the culture zone when agitated.

It can be seen that the settling zone 16 is encompassed by the partition 14, by the conical side wall 12 in the upper region of the tank and additionally, by an annular crown 30 which extends upwardly towards the partition 14 and ends at a distance therefrom leaving a circular slot 31 therebetween. The crown 30 also defines a space which extends above the lamellar elements 20 and below the slot 31.

The partition 14 is provided at its lower portion with a cylindrical apron 32 the purpose of which is to better separate the settling zone from the culture zone as explained in detail hereinbelow.

A supply line 33 of an oxygen-containing gas, or another suitable gas, is connected to the tank 10 at the bottom thereof.

In operation, a cell culture medium is supplied to the tank 10 through the top until it reaches the top level in the cell culture zone 19 indicated by the solid triangle mark. At this point the medium, which also fills the settling zone, starts overflowing from the settling zone through the slot 31. The feed rate of the medium is controlled so as to allow the culture to reach desired cell density and for live cells to sediment in the passageways of the lamellar elements 14 of the settling zone 16. The action of the agitator 22 and the supply rate of the gas from the line are controlled in a well known manner to achieve optimum process conditions.

Figure 2:
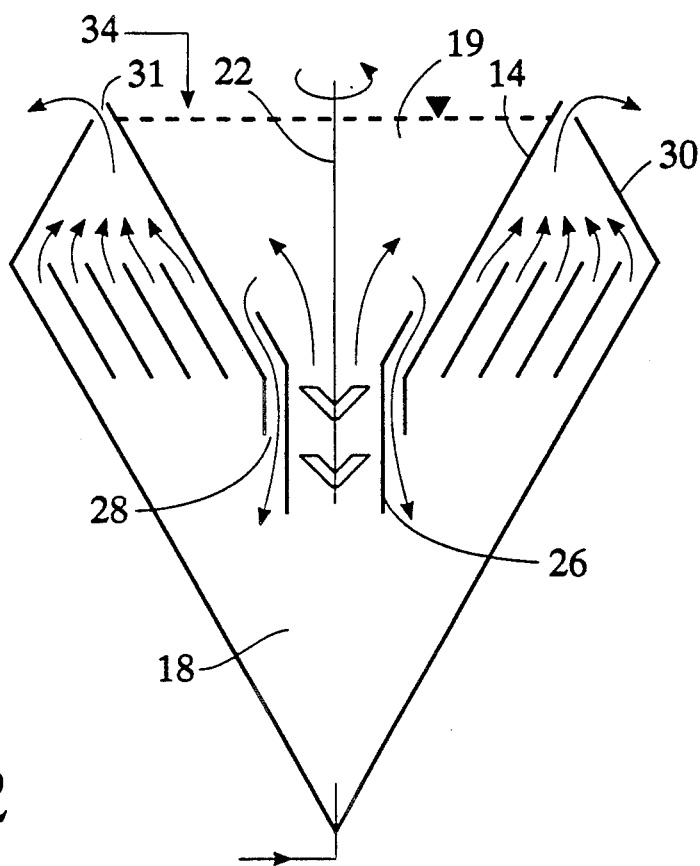
FIG. 2 is an axial cross-section of the embodiment of FIG. 1 illustrating the flow pattern of the culture medium in the apparatus.

FIG. 2 illustrates the flow pattern of the culture medium in the apparatus of FIG. 1. It can be seen that the culture medium is supplied from the line 34 to the open top of the cell culture zone 19 and overflows at the slit 31 between the partition 14 and crown 30. As shown with arrows, the action of agitator 22 causes the culture medium to flow upwards inside draft tube 26 and return to the lower part 18 of the culture zone through downcomer 28.

The provision of apron 32 is intended to separate the downward flow in the downcomer from the upward flow in the adjacent region of the settling zone.

In the absence of the crown 30 (FIGS. 1 and 2), less than the total amount of the medium leaving the upper ends of the lamellar passageways in the settling zone would overflow directly, and the remaining streams would return to the cell culture zone. Such a (hypothetical) flow pattern is undesired and, according to the invention, is virtually eliminated due to the provision of the crown 30 or other means extending the settling zone above top level of the lamellar settling elements 20 (FIG. 1).

The open angle between the side walls of the tank in the embodiment illustrated in the drawings is 60°, but may be different depending on operational and other factors. It will be noted that the volume/surface factor discussed hereinabove changes as the angle is changed which is of importance for scale-up purposes.

It will also be understood that it is not essential that the entire tank has a conical shape (or upwardly diverging walls). While such shape in the settling zone region affords the benefits discussed herein, the conical shape of the lower part of the tank, below the settling zone, is not a prerequisite.

In experiments conducted to validate the invention, the dimensions of the apparatus were as follows:

| | |
|---|---|
| height of the main cone (12) | 19 cm; |
| height of the entrance to the sedimenter | 15 cm, |
| draft tube diameter | 5 cm, |
| downcomer diameter | 7.4 cm, |
| open angle of the cone | 60°, |
| spacing between lamellae (20) | 3.3 mm, |
| volume of the culture zone | 2.7 ltrs. |

The culture medium used was Protein-Free Hybridoma Medium II sold by Gibco. Maximum perfusion rate was 2 volumes per day. The temperature of the culture was 37 deg. C. and the pH was maintained at 6.8. The dissolved oxygen measurements indicated 30% air saturation at 0 psig. The duration of the culture was 29 days and the maximum cell density obtained was 7 million live cells per milliliter.

We claim:

1. An apparatus for perfusion cell culture comprising:
    a cell culture tank having a suspension cell culture zone, a cell settling zone, an opening at the top of the tank for supplying a culture medium to said cell culture zone and an opening for discharging a spent culture medium from said settling zone,
    the settling zone being disposed annularly in the upper portion of the tank co-extensively, in a vertical direction, with a part of the cell culture zone,
    a partition disposed between said zones to enable said zones to communicate with each other only below said partition,
    a centrally disposed substantially cylindrical draft tube extending substantially vertically along at least a part of said cell culture zone to define a passage between said draft tube and the partition,
    wherein the tank has upwardly diverging side walls at least in the upper portion of said tank which houses said settling zone, the partition has upwardly diverging walls substantially parallel to the side walls of the tank thereby defining a generally inversely-frustoconical shape of the settling zone, and
    the settling zone comprises means defining a plurality of angularly disposed passageways of upwardly increasing cross-sectional area, said passageways being substantially parallel to the walls of the tank in the settling zone and to the wall of the partition.

2. The apparatus according to claim 1 wherein said means defining said passageways are interspaced frustoconical nested elements having upwardly diverging surfaces.

3. The apparatus according to claim 1 wherein the outlet from said settling zone is disposed below the level defined by the top of the cell culture zone to enable the culture medium to overflow from the settling zone when supplied to the culture zone, and above the top level of said passageways by a distance facilitating an upward flow of said culture medium through said passageways.

4. The apparatus according to claim 1 wherein said side walls and said partition are substantially conical and parallel to each other and said settling zone is disposed annularly and concentrically relative to said cell culture zone.

5. The apparatus according to claim 1 further comprising agitating means in said cell culture zone for agitating said cell culture medium.

6. The apparatus according to claim 1 further comprising mechanical agitating means within the draft tube operative to cause upward flow of the cell culture medium through said tube.

7. The apparatus according to claim 1 further comprising means for supplying a culture supporting gas to said tank.

8. An apparatus for perfusion cell culture comprising:
    a cell culture tank having a lower region and an upper region, upwardly diverging side walls at least in said upper region, and an opening for supplying a culture medium to said tank,
    an upwardly-diverging tubular partition extending at least over the upper region of said cell culture tank, said partition being substantially parallel to the upwardly diverging side walls of said tank to define an annular, generally inverse-frustoconical cell settling zone therebetween, said cell settling zone having an opening for discharging a spent culture medium therefrom,
    said partition being disposed to enable said settling zone to communicate with the rest of the tank only below said partition, a centrally disposed substantially cylindrical draft tube extending substantially vertically along at least a part of said cell culture zone to define a passage between said draft tube and the partition, wherein the settling zone comprises means defining a plurality of angularly disposed passageways of upwardly increasing cross-sectional area, said passageways being substantially parallel to the walls of the tank and to the partition.

* * * * *